US006952607B2

(12) United States Patent
Mulhauser (10) Patent No.: US 6,952,607 B2
(45) Date of Patent: Oct. 4, 2005

(54) METHOD AND APPARATUS FOR DELIVERING DEFIBRILLATION AND PACING ENERGY FROM A SINGLE POWER SOURCE (75) Inventor: Daniel F. Mulhauser, Windham, NH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 615 days.

(21) Appl. No.: 10/024,763
(22) Filed: Dec. 20, 2001

(65) Prior Publication Data
US 2003/0120310 A1 Jun. 26, 2003

(51) Int. Cl.[7] .............................................. A61N 1/362
(52) U.S. Cl. ................................................. 607/4; 607/7
(58) Field of Search ................................. 607/4, 5, 7, 8

(56) References Cited
U.S. PATENT DOCUMENTS 6,035,235 A    3/2000  Perttu et al. ................... 607/5
6,094,597 A    7/2000  Wold ............................. 607/5
6,104,953 A    8/2000  Leyde ............................ 607/4
6,175,765 B1   1/2001  Sullivan et al. ................ 607/5
6,208,895 B1 * 3/2001  Sullivan et al. ................ 607/4

FOREIGN PATENT DOCUMENTS

WO    WO0021609    4/2000
WO    WO0126731    4/2001    ............ A61N/1/39

* cited by examiner

Primary Examiner—Angela D. Sykes
Assistant Examiner—Roderick Bradford (57) ABSTRACT A defibrillator circuit that delivers high voltage electrical defibrillation pulses and lower energy pacing pulses to a patient. The circuit includes a current regulator which is operative to control the current level applied to the patient. Control circuitry is provided which permits the current regulator to be disabled in the defibrillation mode of operation prior to application of defibrillation pulses. An H-bridge supplies pulses to the patient and the current regulation is provided serially with the H-bridge such that current is regulated regardless of the polarity of pulses applied to the patient.

29 Claims, 5 Drawing Sheets

METHOD AND APPARATUS FOR DELIVERING DEFIBRILLATION AND PACING ENERGY FROM A SINGLE POWER SOURCE

CROSS REFERENCE TO RELATED APPLICATIONS

Not Applicable

BACKGROUND OF THE INVENTION

1. Field of the Invention

This invention relates to a method and apparatus for delivering electrical energy to a patient for maintaining and/or restoring the pumping rhythm of a heart, and more particularly to a method and apparatus for regulating a current flow to the patent to conform with a predetermined maximum value and/or according to a predetermined waveform. A single power source is provided to deliver current with either pacing or defibrillation energy.

2. Description of the Related Art

The frequent occurrence of sudden cardiac arrest (SCA) is well known. SCA occurs when the heart stops pumping blood, usually due to abnormal electrical activity in the heart, such as for example, ventricular fibrillation, which is caused very fast electrical activity in the heart. Ventricular fibrillation is treated by applying an electric shock to the patient's heart through the use of a defibrillator. Other forms of abnormal cardiac rhythms, such as bradycardia (slow heart rate) and tachycardia (rapid heart rate) may be treated with a low voltage pacing pulse, which assists the heart's natural pacemakers. Devices which accomplish both defibrillation and pacing typically include two power sources, two capacitors, and two control mechanisms, one for the high energy defibrillation pulse and one for the lower energy pacing pulses. This double circuitry ultimately increases the weight size, and cost of the device.

There is a need for an apparatus which performs both defibrillation and pacing and which uses a single power source, a single high energy capacitor and a single control mechanism to deliver either defibrillation or pacing energy.

SUMMARY OF THE INVENTION

The present invention is a defibrillator-pacer for delivering electrical energy to a patient as either defibrillation pulses or pacing pulses. The defibrillator-pacer comprises a power source, an H-bridge comprising a plurality of switches which control the delivery of the electrical energy from the power source to the patient; and a current control circuit which regulates electrical current supplied to the patient, wherein the current control circuit is serially connected with the H-bridge. The current control circuit regulates the current in response to a current control signal as determined by a controller. The current control signal may be a constant value or a time varying signal having a predetermined or varying waveform. The current control circuit is operable such that the current control signal has a first value where a first pair of switches of the H-bridge is operated and a second value where a second pair of the switches of the H-bridge is operated. The circuit is also operable wherein the current control signal has a waveform of a first shape where a first pair of the switches of the H-bridge is operated and a waveform of a second shape where a second pair of the switches of the H-bridge is operated. Various shapes of the control signal waveform may include sinusoidal, rectangular and truncated exponential waveforms. The current control circuit is also operable as a switch which may be operated prior to the operation of either pair of H-bridge switches. The H-bridge switches are operable in conjunction with the current control circuit to deliver a controlled current biphasic pulse to the patient.

A defibrillator-pacer incorporating the inventive circuit comprises a storage circuit having first and second terminals, the storage circuit operable to store electrical energy; an H-bridge circuit, coupled to the first terminal of the storage circuit, adapted to couple with the patient and operable to deliver electrical current from the stored electrical energy to the patient; and a current control circuit, coupled with the H-bridge circuit and operable to electrically connect the H-bridge circuit with the second terminal of the storage circuit, to regulate the delivery of the electrical current to the patient. The current control circuit, which is operable in a linear mode and responsive to a control voltage, comprises an amplifier, a transistor and a resistor arranged as a voltage to current follower. A controller controls the H-bridge to control the polarity of the electrical current delivered to the patient and determines the control voltage as a fixed value or a time varying waveform, which may be, for example, a sinusoidal waveform, a half-sinusoidal waveform, a rectangular waveform or a decaying exponential waveform.

In a first alternate embodiment of the current control circuit, a first transistor, an amplifier and a resistor are arranged as a voltage to current follower to control the current through the patient according to a predetermined scale factor determined by the resistor and a first control voltage, and a second transistor is arranged to selectively bypass the first resistor in response to a second control voltage to change the scale factor of the voltage to current follower.

In a second alternate embodiment of the control circuit, a first resistor is connected in series with the H-bridge to passively limit the current through the patient. A first transistor, an amplifier and a second resistor are arranged as a voltage to current follower to control the current through the patient according to a predetermined scale factor determined by the first resistor, the second resistor and a first control voltage. A second transistor bypasses the first resistor in response to a second control voltage to change the scale factor of the voltage to current follower and a third transistor bypasses the second resistor in response to a third control voltage to further change the scale factor of the voltage to current follower.

BRIEF DESCRIPTION OF THE DRAWINGS

The present invention will become more apparent and more readily appreciated from the following description of the various embodiments, taken in conjunction with the accompanying drawings in which.

DETAILED DESCRIPTION OF THE INVENTION

Reference will now be made in detail to the present embodiments of the present invention, examples of which are illustrated in the accompanying drawings, wherein like reference numerals refer to like elements throughout.

The present invention is operable in a first mode which provides either a high energy monophasic or a biphasic electrical pulse to a patient via electrodes applied to the chest of a patient and operable in a second mode which provides lower energy pacing pulses to the patient. Monophasic defibrillators deliver an electrical current pulse of a single polarity. Biphasic defibrillators deliver an electrical current pulse of a first polarity followed by an electrical current pulse of the opposite polarity. Where delivered external to the patient, these electrical pulses are high energy (typically in the range of 30 J to 360 J). The present invention may be employed by defibrillators or pacers intended to generate monophasic, biphasic or multiphasic waveforms and may be employed by defibrillators that allow the user to select the waveform type. Finally, the present invention may be employed in either external or implantable defibrillators or pacers. It is believed that the invention described herein is primarily beneficial for defibrillators that combine defibrillation with pacing.

Figure 1:
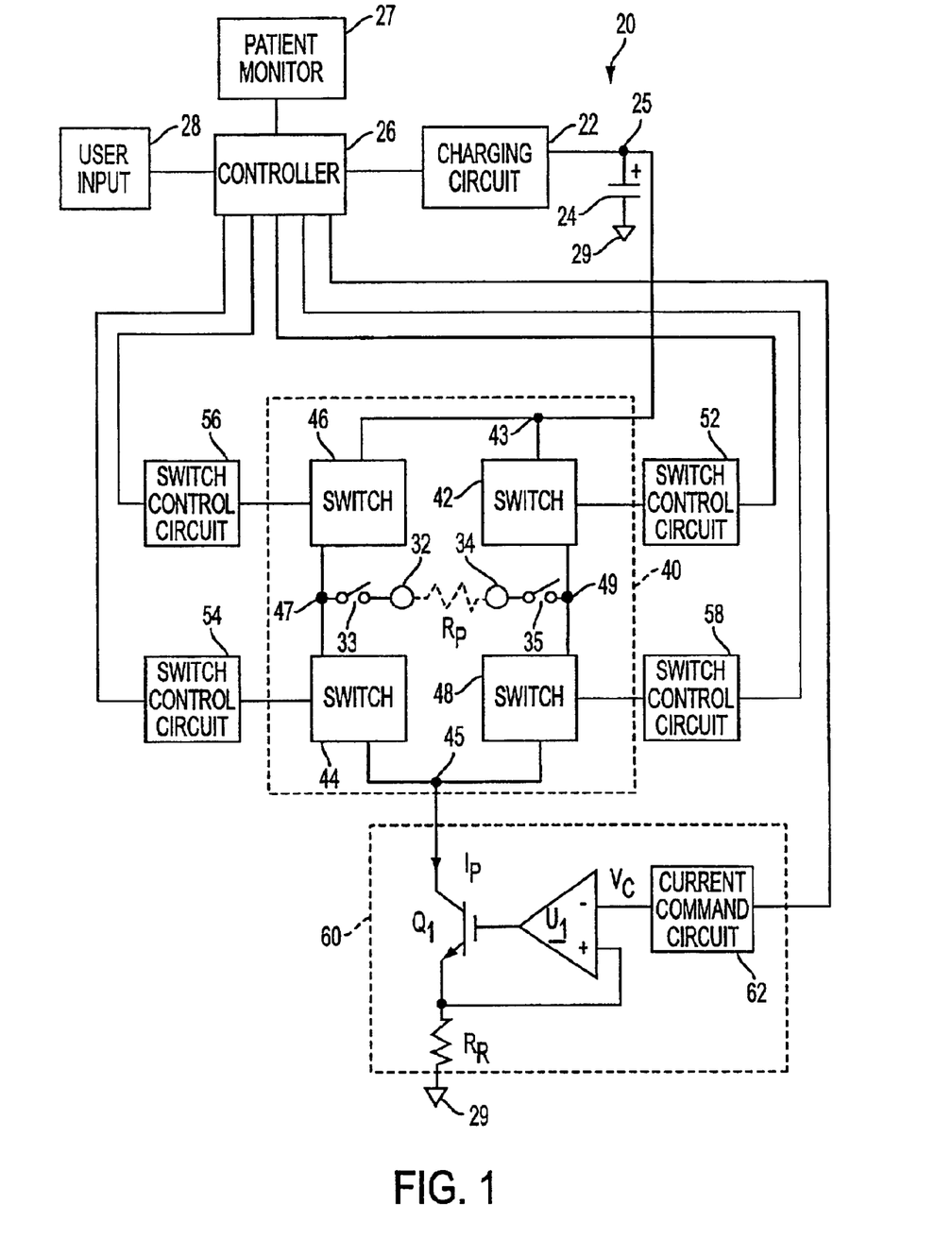
FIG. 1 is a functional block diagram illustrating a defibrillator-pacer circuit according to an embodiment of the present invention.

FIG. 1 is a functional block diagram illustrating a defibrillator-pacer 20 comprising a charging circuit 22, a storage capacitor 24, a controller 26, such as for example a micro-controller or a processor (hereinafter controller 26), a user input section 28, output electrodes 32 and 34, an H-bridge 40 and a current control circuit 60. The defibrillator-pacer 20 is powered by an energy source such as a removable battery (not shown). The controller 26 controls overall operation of the various components of the defibrillator-pacer 20. The H-bridge 40 delivers a pulse of electrical energy to a patient via electrodes 32 and 34 under the control of controller 26. The defibrillator-pacer 20 comprises other well known components which contribute to the overall operation of the defibrillator-pacer 20, such as for example, a patient monitor 27, which acquires and processes the patient's electrocardiogram (ECG) signals, and sends the patient's ECG signals to the controller 26. The controller 26 controls at least one of timing, amplitude, polarity and shape of energy pulses applied to the patient according to the various modes of operation of the defibrillator-pacer 20. Components which are well known and which are not necessary to the understanding of the present invention are not shown in order to avoid obscuring the embodiments of the invention.

The H-bridge 40 comprises switches 42, 44, 46 and 48 which are driven by switch control circuits 52, 54, 56 and 58, respectively. The switch control circuits 52, 54, 56 and 58 are controlled in turn by the controller 26. The switches 42 and 46 have a common connection at a node 43 which is connected to a positive (+) terminal 25 of storage capacitor 24. The storage capacitor 24 has a negative (−) terminal connected to circuit common 29. The switches 44 and 48 have a common connection at a node 45 which is also a first node of the current control circuit 60. A second node of the current control circuit 60 is connected to the circuit common 29. The current control circuit 60 receives input commands from the controller 26. The switches 44 and 46 have a common connection at a node 47 which is also connected with the electrode 32 and the switches 42 and 48 have a common connection at a node 49 which is also connected to the electrode 34. A resistor RP shown between electrodes 32 and 34 represents the effective resistance of the patient. Switch contacts 33 and 35 are operable to connect the defibrillator-pacer to the patient. The switch contacts 33 sand 35 are preferably contacts of a relay which operates under control of the controller 26.

Figure 2A:
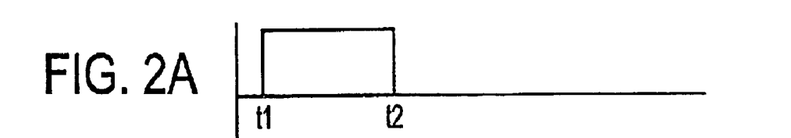
FIGS. 2A–2F are waveforms illustrating delivery of a current where the circuit shown in FIG. 1 is operated in an unregulated mode.
Figure 2B:
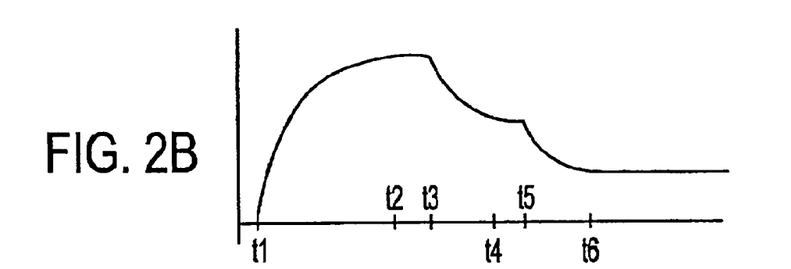
Figure 2C:
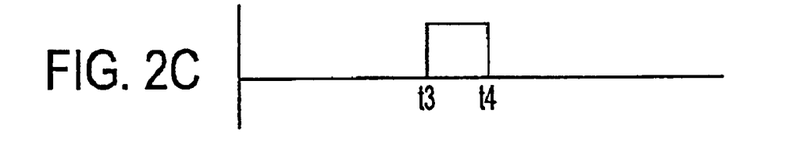
Figure 2D:
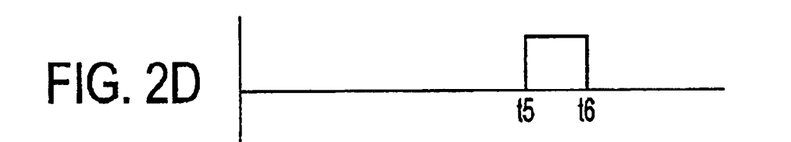
Figure 2E:
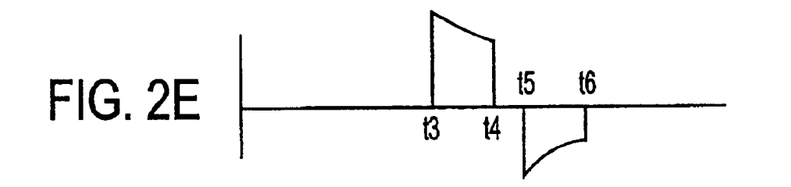
Figure 2F:
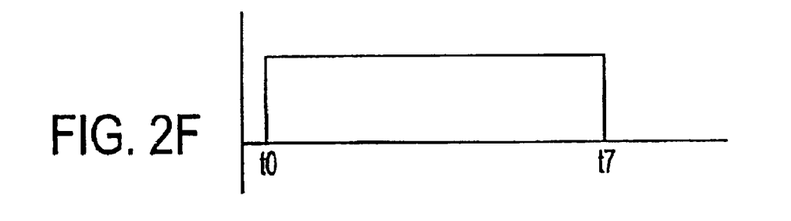

Referring now to FIGS. 2A–2F, one mode of operation of the circuit shown in FIG. 1 will be described. The controller 26 controls the charging circuit 22 in response to an input from the patient monitor 27 or the user input 28, causing the charger to operate for a time interval $t_1$–$t_2$ as shown in FIG. 2A. The charging circuit 22 charges the storage capacitor 24 during the time interval $t_1$–$t_2$ as shown in FIG. 2B to a relative high value, such as for example, 1500 to 2000 volts DC. At the time $t_2$, the charging circuit 22 discontinues charging the storage capacitor 24 and the voltage of capacitor 24 with respect to circuit common 29 remains at a constant value during a time interval $t_2$–$t_3$.

Where the defibrillator-pacer 20 is operated as a defibrillator in a biphasic mode, the controller 26 instructs switch control circuits 52 and 54 to turn on switches 42 and 44, respectively, and instructs the current control circuit 60 to connect node 45 to node 29 either via a fixed low impedance path or to regulate the current passing through the patient. Although current regulation presently has little known value at high energy defibrillation discharges, and may be impractical dissipation wise with current known technology, current regulation of low energies of up to 2 joules is believed to be both practical and beneficial. Switches 42 and 44 are turned on for the time interval $t_3$–$t_4$ as shown in FIG. 2C and where the current control circuit 60 is operating as a fixed low impedance path, current is delivered to the patient $R_P$ via the electrodes 32 and 34 as a decaying exponential waveform according to the patient resistance $R_P$ during the time interval $t_3$–$t_4$ as shown in FIG. 2E.

During a time interval $t_4$–$t_5$, the voltage across the storage capacitor remains at a relatively constant reduced value. At the time $t_5$, the controller 26 again instructs the current control circuit 60 to connect node 45 to node 29 either via the fixed low impedance path or to regulate the current passing through the patient and instructs switch control circuits 56 and 58 to turn on switches 46 and 48, respectively, during a time interval $t_5$–$t_6$ as shown in FIG. 2D. During the time interval $t_5$–$t_6$, the direction of the current applied to the patient via the electrodes 32 and 34 is reversed from the direction previously applied during the time interval $t_3$–$t_4$. Where the current control circuit 60 connects node 45 to node 29 via the fixed low impedance path, current is applied to the patient $R_P$ at electrodes 32 and 34 as a decaying exponential waveform during the interval $t_5$–$t_6$ according to the patient resistance $R_P$ as shown in FIG. 2E.

Alternately, the current control circuit 60 may be commanded to connect node 45 to node 29 at a time $t_0$, such as for example, before the beginning of the charging of the capacitor 24 (before the time $t_1$) or before switches 42 and 44 are turned on at the time $t_3$. Where the control circuit 60 connects nodes 45 and 29 before the voltage across the capacitor 24 exceeds a predetermined value, the stress on components of the current control circuit 60 is significantly reduced, contributing to increased reliability and where a high voltage insulated gate bipolar transistor (IGBT) is used in the H-bridge for commutation, parts with lower voltage ratings may be used in the current control circuit 60, thus again contributing to lower cost.

Where the current regulating circuit 60 is operated in the fixed low impedance mode, the maximum current applied to the patient is determined by the amplitude of the voltage across the capacitor 24, the effective resistance $R_P$ of the patient and the effective impedance of the fixed low impedance path of the current control circuit 60.

Figure 3A:
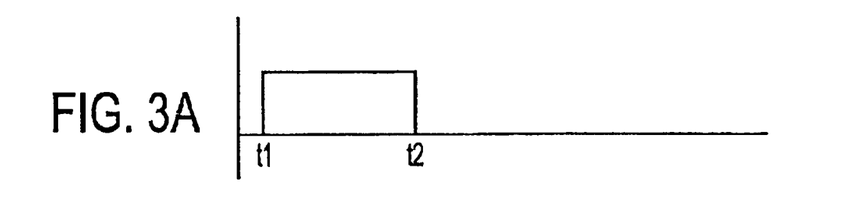
FIGS. 3A–3E are waveforms illustrating delivery of a current where the circuit shown in FIG. 1 is operated in a current regulated mode.
Figure 3B:
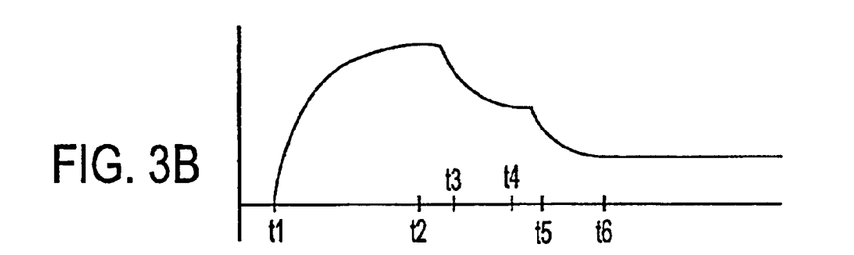
Figure 3C:
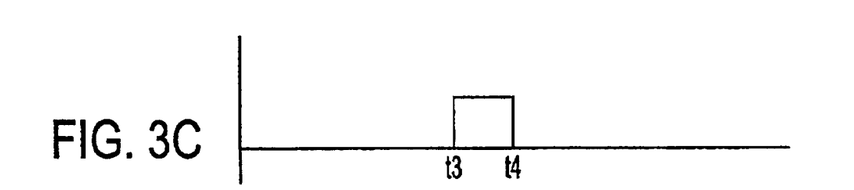
Figure 3D:
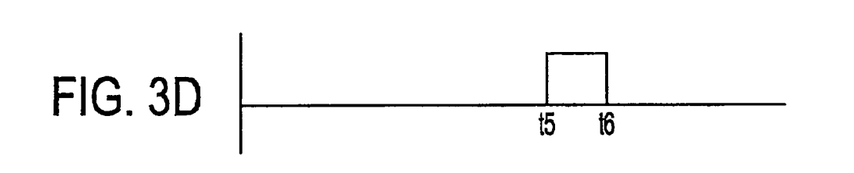
Figure 3E:
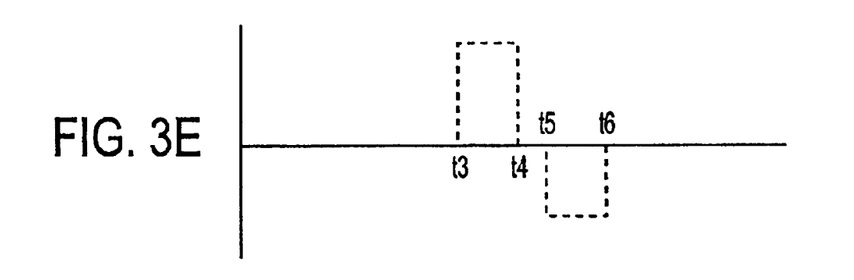

Referring now to FIGS. 3A–3D, the operation of the circuit shown in FIG. 1 will be further described relative to operation in a pacing mode. The controller 26 controls the charging circuit 22 in response to an input from the patient monitor 27 and the charging circuit 22 charges the storage capacitor 24 during a time interval $t_1$–$t_2$ as shown in FIGS. 3A and 2C to a relative low value, such as for example, 75 to 200 volts DC, which may vary dynamically in order to reduce power consumption. At the time $t_2$, the charging circuit 22 discontinues charging the storage capacitor 24 and the voltage at node 25 of capacitor 24 with respect to circuit common 29 remains at a constant value during an interval $t_2$–$t_3$.

Where the defibrillator-pacer is operated as a pacer in a biphasic mode, the controller 26 instructs switch control circuits 52 and 54 to turn on switches 42 and 44, respectively, and instructs the current control circuit 60 to connect node 45 to node 29 and to regulate the current passing through the patient so as not to exceed a predetermined maximum value. Switches 42 and 44 are turned on for a time interval $t_3$–$t_4$ as shown in FIG. 3C and current is delivered to the patient $R_P$ at electrodes 32 and 34 according to the control of the current control circuit 60 and in a first polarity during the interval $t_3$–$t_4$ as shown in FIG. 3E. At a time $t_5$, the controller 26 again instructs the current control circuit 60 to connect node 45 to node 29 and to regulate the current passing through the patient and instructs switch control circuits 56 and 58 to turn on switches 46 and 48, respectively, during a time interval $t_5$–$t_6$ as shown in FIG. 3D, reversing the direction of current applied to the patient from the direction previously applied during the time interval $t_3$–$t_4$. The reversed polarity waveform is indicated during the time interval $t_5$–$t_6$ as shown in FIG. 3E. In FIG. 3E, the current waveforms applied to the patient for the time intervals $t_3$–$t_4$ and $t_5$–$t_6$ are indicated as broken lines, since the shape of the waveform will depend on the character of the current control command, as will be explained more fully below.

Referring again to FIG. 1, the current control circuit 60 comprises a transistor Q1, a resistor $R_R$, an amplifier U1, and a current command circuit 62. Resistor $R_R$ has a first end connected to circuit common 29 and a second end connected to the emitter of transistor Q1. The collector of transistor Q1 is connected to the H-bridge at the node 45. The gate of transistor Q1 is connected to the output of amplifier U1 and the non-inverting input (+) of amplifier U1 is connected to the second end of resistor $R_R$ so as to form a current follower circuit wherein the current through resistor $R_R$ follows the voltage applied at the inverting input (–) of amplifier U1, thus the patient current $I_P$ becomes $V_C$ divided by $R_P$, where $V_C$ is the voltage at the inverting input of amplifier U1. Thus, the current through the patient is regulated according to the voltage $V_C$ applied at the inverting input of amplifier U1. The current command interface circuit 62 receives commands from the controller 26 and outputs either a fixed value as $V_C$ or a time variant value of $V_C$ according to a desired mode of operation of the defibrillator-pacer 20.

During operation of the defibrillator-pacer where patient current is being controlled by the current control circuit 60, the charging circuit 22 continuously or periodically replenishes the charge on capacitor 24 to ensure that the voltage at node 25 is sufficiently high to maintain the voltage of the waveform commanded by the time variant $V_C$. Where it is desired to operate the defibrillator-pacer 20 wherein node 45 is connected to node 29 via the fixed low impedance path, the value $V_C$ is determined so that transistor Q1 effectively operates as a switch. Where it is desired to operate the defibrillator-pacer 20 so that the current regulating circuit 60 controls the current passing between nodes 45 and 29, the values of resistor $R_R$ and input voltage $V_C$ are determined so that Q1 remains in an active region for desired values of patient current. Where Q1 remains in the active region, the polarity of current applied to the patient is controlled by the H-bridge and the amplitude and waveform of current applied to the patient are controlled by the current regulating circuit 60.

Referring to FIGS. 4A–4E, an example of operation of the pacer-defibrillator 20 in a current regulation mode is illustrated. For simplicity of explanation, the voltage across capacitor 24 is assumed to be charged and held at a constant value. It will be readily recognized by persons skilled in the art that if the voltage across capacitor 24 is not maintained at a constant value, that is, allowed to decay as a function of current delivered, the waveform applied to the patient may vary, however, the maximum amplitude of current applied to the patient will still be controlled by the current regulator 60.

Figure 4A:
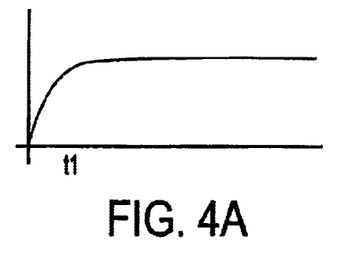
FIGS. 4A–4J are waveforms illustrating delivery of a current where the circuit shown in FIG. 1 is operated in a current regulated mode from a power source having a constant value.
Figure 4B:
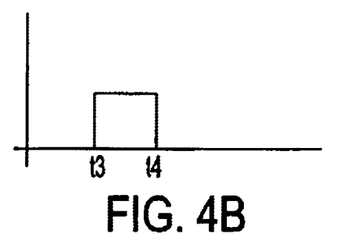
Figure 4C:
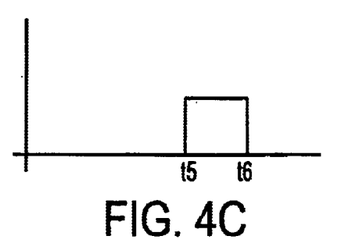
Figure 4D:
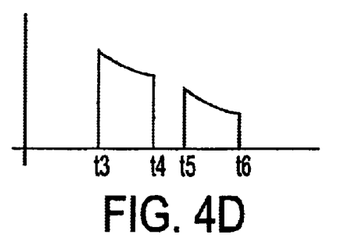
Figure 4E:
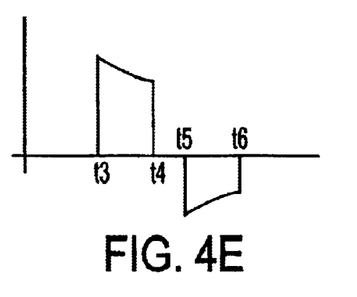
Figure 4F:
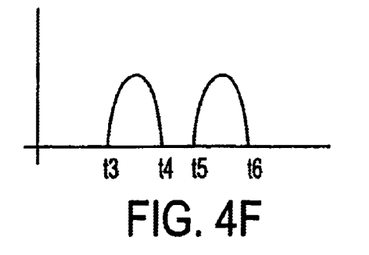
Figure 4G:
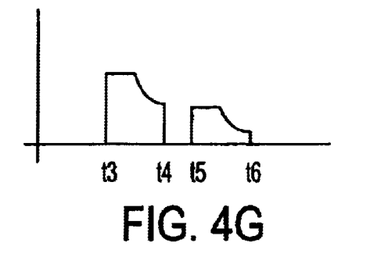
Figure 4H:
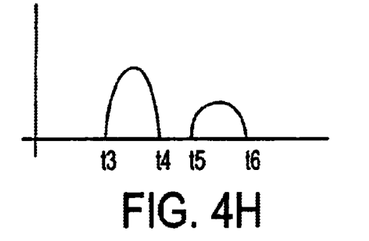
Figure 4I:
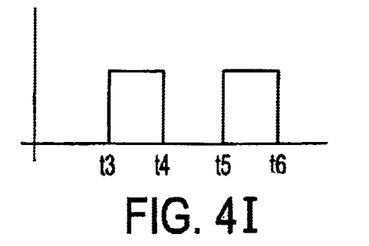
Figure 4J:
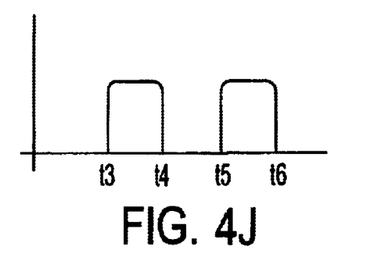

As shown in FIG. 4A, the voltage across capacitor 24 is charged to a constant value at a time $t_1$. At a time interval $t_3$–$t_4$ indicated in FIG. 4B, the controller 26 causes the switches 42 and 44 to close, determining the polarity of a pulse to be delivered to the patient. The controller 26 also causes the current command circuit 62 to provide the waveform indicated in FIG. 4D at the time interval $t_3$–$t_4$ to be applied to the inverting input of amplifier U1, thus applying a current to the patient $R_P$ during the time interval $t_3$–$t_4$ of the waveform as shown in FIG. 4E. Next, at a time interval $t_5$–$t_6$ as indicated in FIG. 4C, the controller 26 causes the switches 46 and 48 to close, determining the polarity of the pulse to be delivered to the patient to be opposite the polarity of the pulse previously applied during the time interval $t_3$–$t_4$. The controller 26 concurrently causes the current command circuit 62 to provide the waveform indicated in FIG. 4D at the time interval $t_5$–$t_6$ to be applied to the inverting input of amplifier U1, thus applying a current of the waveform shown in FIG. 4E at the time interval $t_5$–$t_6$ to the patient who is represented by the resistance $R_P$. Where Q1 is operated so as to remain in a linear region, the current waveform $I_P$ through the patient $R_P$ will follow the voltage waveform $V_C$. Thus, current waveforms, such as for example, a one-half sine waveform, FIG. 4F, a truncated exponential waveform, FIG. 4G, a damped sine waveform, FIG. 4H, a rectangular waveform, FIG. 4I, and a rounded rectangle waveform, FIG. 4J may be generated. A person skilled in the art will recognize that where a controlled current mono-phasic waveform is desired, the controller 26 may be appropriately programmed to cause only one of switch pair 42 and 44 or switch pair 46 and 48 to close and to cause an appropriate voltage waveform to be applied as $V_C$. Thus, both monophasic and biphasic pulses are regulated by the present invention.

Transistor Q1 is preferably an insulated gate bipolar transistor (IGBT). A transistor having a lower voltage rating, such as for example a field effect transistor (FET) or a junction type bipolar transistor, may be used where it is not desired to regulate the current in the defibrillation mode or where a high voltage IGBT is used in the H-bridge for commutation. Where a transistor having a lower voltage rating is used, transistor Q1 is preferably operated as a switch and fully turned on before the capacitor 24 is charged to high voltages and remain fully turned on until the capacitor has been discharged.

Figure 5:
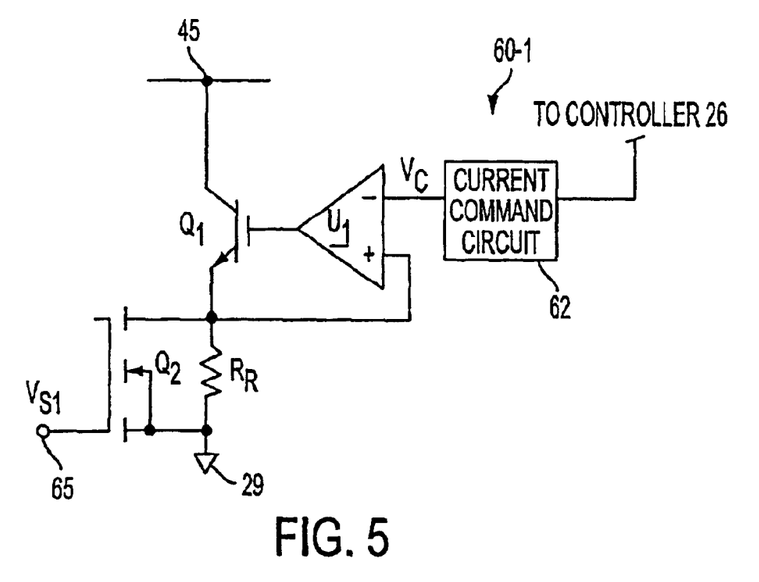
FIG. 5 is an schematic diagram of an alternate construction of a current regulating portion of the defibrillator-pacer circuit shown in FIG. 1.

Preferably, the sense resistor $R_R$ in the current regulating circuit 60 of FIG. 1 is selected to optimize regulation of low level pacing pulses. In the fixed low impedance mode, it is advantageous to bypass the resistor $R_R$ in the current regulating circuit 60 shown in FIG. 1. Referring now to FIG. 5, a current regulating circuit 60-1 which includes a circuit arrangement for bypassing the resistor $R_R$ is illustrated. The current regulating circuit 60-1 operates in a similar manner as the current regulating circuit 60, however the current regulating circuit comprises a transistor Q2 which performs a bypass of the resistor $R_R$ and an additional node 65 which receives an input voltage $V_{S1}$ to operate the bypass. The transistor Q2 is preferably a power field effect transistor having a source and a drain connected across the resistor $R_R$ and a gate connected to the node 65. A voltage rating in the 20 to 50 volt range is adequate for the transistor Q2.

Figure 6:
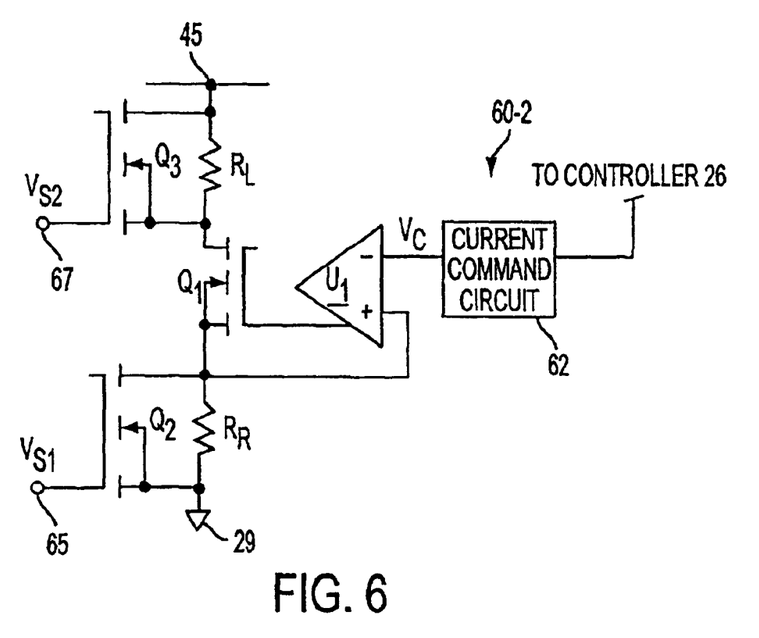
FIG. 6 is an schematic diagram of another alternate construction of a current regulating portion of the defibrillator-pacer circuit shown in FIG. 1.

Referring now to FIG. 6, a current regulating circuit 60-2 includes a circuit arrangement for bypassing the resistor $R_R$ and a series limiting resistor is illustrated. The current regulating circuit 60-2 operates in a similar manner as the current regulating circuit 60, however the current regulating circuit 60-2 further comprises a transistor Q2 which performs a bypass of the resistor $R_R$, an additional node 65 which receives an input voltage $V_{S1}$ to operate the bypass of $R_R$, a series limiting resistor $R_L$, a transistor Q3 which bypasses the resistor $R_L$ and a node 67 which receives a voltage $V_{S2}$ which operates the bypass of $R_L$. The transistor Q2 is preferably a power field effect transistor having a source and a drain connected across the resistor $R_R$ and a gate connected to the node 65. A voltage rating of transistor Q2 in the 20 to 50 volt range is adequate. The series limiting resistor $R_L$ is inserted between the collector of Q1 and the node 45. The series resistor $R_L$ is used where it is desirable to have additional limiting, such as for example, in the pacer mode. The transistor Q3 performs a bypass of the resistor $R_L$ in response to an input voltage $V_{S2}$ received at node 67. The transistor Q3 is preferably a power field effect transistor having a source and a drain connected across the resistor $R_L$ and a gate connected to the node 67. A voltage rating of transistor Q3 should be in the 50 to 200 volt range or higher. Where it is desirable to bypass both the resistors $R_L$ and $R_R$ simultaneously, the voltage $V_{S1}$ should be applied before the voltage $V_{S2}$ so that a ground reference is established for the transistor Q3. Otherwise, a more complex gate drive for the transistor Q3 is required. Where the circuit configuration of FIG. 6 is employed, switches 44 and 48 (FIG. 1) are high voltage switching components. Where the switches 44 and 48 of the H-bridge are high voltage switching components, Q1 may be a MOSFET having a voltage range of 200 volts or greater.

Defibrillator-pacers incorporating the present invention may also incorporate additional circuitry (not shown) which avoids application of the capacitor voltage to the H-bridge components during standby operations or which disconnects the patient from the outputs of the H-bridge during standby operations, such as for example, a relay may be incorporated between the patient and the H-bridge.

Although a few embodiments of the present invention have been shown and described, it will be appreciated by those skilled in the art that changes may be made in these embodiments without departing from the principles and spirit of the invention, the scope of which is defined in the claims and their equivalents.

What is claimed is:

1. A circuit for delivering electrical energy as one of defibrillation pulses and pacing pulses to a patient, the circuit comprising:
   a power source;
   an H-bridge comprising a plurality of switches which control the delivery of the electrical energy from the power source to the patient; and
   a current control circuit which regulates electrical current supplied to the patient, the current control circuit serially connected with the H-bridge.

2. The circuit according to claim 1, wherein the current control circuit regulates the current in response to a current control signal.

3. The circuit according to claim 2, wherein the current control signal is a waveform having a shape of a desired current waveform to be delivered to the patient.

4. The circuit according to claim 3, wherein the current control waveform has a first shape where a first pair of the plurality of switches is operated and a second shape where a second pair of the plurality of switches is operated.

5. The circuit according to claim 4, wherein the shapes of the first and second waveforms are truncated exponential waveforms.

6. The circuit according to claim 4, wherein the shapes of the first and second waveforms are half sinusoidal.

7. The circuit according to claim 4, wherein the shapes of the first and second waveforms are rectangular.

8. The circuit according to claim 3, wherein the shape of the control signal waveform is a truncated exponential waveform.

9. The circuit according to claim 3, wherein the shape of the control signal waveform is half sinusoidal.

10. The circuit according to claim 3, wherein the shape of the control signal waveform is rectangular.

11. The circuit according to claim 2, wherein the current control signal is a dc value.

12. The circuit according to claim 2, wherein the current control signal has a first value where a first pair of the plurality of switches is operated and a second value where a second pair of the plurality of switches is operated.

13. The circuit according to claim 1, wherein the current control circuit operates as a switch prior to an operation of the plurality of switches.

14. The circuit according to claim 13, wherein the plurality of switches and the current control circuit are operated to deliver the electrical energy as a biphasic pulse to the patient.

15. A defibrillator-pacer for delivering electrical energy to a patient, the defibrillator-pacer comprising:
   a storage circuit having first and second terminals, the storage circuit operable to store electrical energy;
   an H-bridge circuit, coupled to the first terminal of the storage circuit, adapted to couple with the patient and operable to deliver electrical current from the storage circuit energy to the patient; and
   a current control circuit, coupled with the H-bridge circuit and operable to electrically connect the H-bridge circuit with the second terminal of the storage circuit, to regulate the delivery of the electrical energy to the patient.

16. The defibrillator-pacer according to claim 15, wherein the current control circuit operates in a linear mode and responsive to a control voltage.

17. The defibrillator-pacer according to claim 16, further comprising:
a controller which:
controls the H-bridge to control the polarity of the electrical current delivered to the patient; and
determines the control voltage.

18. The defibrillator-pacer according to claim 17, wherein the control voltage is a fixed value.

19. The defibrillator-pacer according to claim 17, wherein the control voltage has a time varying waveform.

20. The defibrillator-pacer according to claim 19, wherein the time varying waveform is a sinusoidal waveform.

21. The defibrillator-pacer according to claim 19, wherein the time varying waveform is a decaying exponential waveform.

22. The circuit according to claim 19, wherein the time varying waveform is a half sinusoidal waveform.

23. The circuit according to claim 19, wherein the time varying waveform is a rectangular waveform.

24. The circuit according to claim 19, wherein the time varying waveform is a rounded rectangular waveform.

25. The circuit according to claim 19, wherein the time varying waveform is a damped sinusoidal waveform.

26. The defibrillator-pacer according to claim 15, wherein the current control circuit comprises an amplifier, a transistor and a resistor arranged as a voltage to current follower.

27. A defibrillator-pacer for delivering electrical energy to a patient, the defibrillator-pacer comprising:
a storage circuit having first and second terminals, the storage circuit operable to store electrical energy;
an H-bridge circuit, coupled to the first terminal of the storage circuit, adapted to couple with the patient and operable to deliver electrical current from the storage circuit energy to the patient; and
a current control circuit, coupled with the H-bridge circuit and operable to electrically connect the H-bridge circuit with the second terminal of the storage circuit, to regulate the delivery of the electrical energy to the patient, the control circuit comprising:
a first transistor, an amplifier and a resistor arranged as a voltage to current follower which controls the current through the patient according to a predetermined scale factor determined by the resistor and a first control voltage, and
a second transistor which bypasses the first resistor in response to a second control voltage to change the scale factor of the voltage to current follower.

28. A defibrillator-pacer for delivering electrical energy to a patient, the defibrillator-pacer comprising:
a storage circuit having first and second terminals, the storage circuit operable to store electrical energy;
an H-bridge circuit, coupled to the first terminal of the storage circuit, adapted to couple with the patient and operable to deliver electrical current from the storage circuit energy to the patient; and
a current control circuit, coupled with the H-bridge circuit and operable to electrically connect the H-bridge circuit with the second terminal of the storage circuit, to regulate the delivery of the electrical energy to the patient, the control circuit comprising:
a first resistor connected in series with the H-bridge which limits the current through the patient;
a first transistor, an amplifier and a second resistor arranged as a voltage to current follower which controls the current through the patient according to a predetermined scale factor determined by the first resistor, the second resistor and a first control voltage,
a second transistor which bypasses the first resistor in response to a second control voltage to change the scale factor of the voltage to current follower.

29. The defibrillator-pacer according to claim 28, wherein the control circuit further comprises:
a third transistor which bypasses the second resistor in response to a third control voltage to further change the scale factor of the voltage to current follower.

* * * * *